(12) United States Patent
Janski et al.

(10) Patent No.: US 8,246,549 B2
(45) Date of Patent: Aug. 21, 2012

(54) METHOD FOR PREDICTING STROKE AND PAIN IN A HUMAN PATIENT

(75) Inventors: Alvin Janski, Chesterfield, MO (US); Joe Martinosky, Wildwood, MO (US)

(73) Assignee: Everest Biomedical Instruments Co., Chesterfield, MO (US)

( * ) Notice: Subject to any disclaimer, the term of this patent is extended or adjusted under 35 U.S.C. 154(b) by 1701 days.

(21) Appl. No.: 10/588,221

(22) PCT Filed: Jan. 28, 2005

(86) PCT No.: PCT/US2005/003398
§ 371 (c)(1),
(2), (4) Date: Jul. 27, 2006

(87) PCT Pub. No.: WO2005/072618
PCT Pub. Date: Aug. 11, 2005

(65) Prior Publication Data
US 2007/0142740 A1    Jun. 21, 2007

Related U.S. Application Data

(60) Provisional application No. 60/540,146, filed on Jan. 29, 2004, provisional application No. 60/540,242, filed on Jan. 29, 2004.

(51) Int. Cl.
*A61B 5/08* (2006.01)
*G01N 33/497* (2006.01)
(52) U.S. Cl. .......................... 600/532; 73/23.3
(58) Field of Classification Search .......... 600/529–543, 600/484; 73/23.3
See application file for complete search history.

(56) References Cited

U.S. PATENT DOCUMENTS

| | | | | |
|---|---|---|---|---|
| 5,922,610 | A  * | 7/1999 | Alving et al. | 436/116 |
| 6,221,026 | B1 * | 4/2001 | Phillips | 600/532 |
| 6,244,096 | B1 * | 6/2001 | Lewis et al. | 73/23.2 |
| 6,248,078 | B1 * | 6/2001 | Risby et al. | 600/529 |
| 6,416,479 | B1   | 7/2002 | Seidman | |
| 6,428,483 | B1 * | 8/2002 | Carlebach | 600/532 |
| 6,461,306 | B1 * | 10/2002 | Hanson et al. | 600/532 |
| 6,467,333 | B2 * | 10/2002 | Lewis et al. | 73/31.05 |
| 6,540,691 | B1 * | 4/2003 | Phillips | 600/532 |
| 6,582,376 | B2 * | 6/2003 | Baghdassarian | 600/543 |
| 6,599,253 | B1 * | 7/2003 | Baum et al. | 600/532 |
| 6,612,306 | B1 * | 9/2003 | Mault | 128/204.22 |
| 6,620,109 | B2 * | 9/2003 | Hanson, III | 600/532 |
| 6,656,127 | B1 * | 12/2003 | Ben-Oren et al. | 600/532 |

(Continued)

OTHER PUBLICATIONS

K. Sylvester, R. Patey, J. Hall, G. Fafferty, M. Dick, S.L. Thein, A. Greenough, "Measurement of exhales carbon monoxide in children with sickle cell disease", Presentation abstract published in European Respiratory Journal 2002, Supplement 38, p. 139, London, United Kingdom, Presented at ERS Annual Congress, Stockholm, Sep. 15, 2002.

(Continued)

*Primary Examiner* — Navin Natnithithadha
(74) *Attorney, Agent, or Firm* — Howard & Howard Attorneys PLLC

(57) ABSTRACT

A method for predicting the onset of any (NO)-related negative influence of hemolysis, such as pain or the likely occurrence of a stroke, in a human patient by detecting abnormal levels of hemolysis, through the measurement of one or more breath gas concentrations.

3 Claims, 4 Drawing Sheets

U.S. PATENT DOCUMENTS

| | | | |
|---|---|---|---|
| 6,712,770 B2 * | 3/2004 | Lin et al. | 600/532 |
| 6,841,391 B2 * | 1/2005 | Lewis et al. | 436/149 |
| 7,014,612 B2 * | 3/2006 | Hubbard et al. | 600/532 |
| 7,052,468 B2 * | 5/2006 | Melker et al. | 600/532 |
| 7,101,340 B1 * | 9/2006 | Braun | 600/532 |
| 7,255,677 B2 * | 8/2007 | Burch et al. | 600/300 |
| 7,575,553 B2 * | 8/2009 | Stahmann et al. | 600/528 |

OTHER PUBLICATIONS

Written Opinion of the International Searching Authority corresponding to International Application No. PCT/US05/03398.

Search Report corresponding to International Application No. PCT/US05/03398.

* cited by examiner

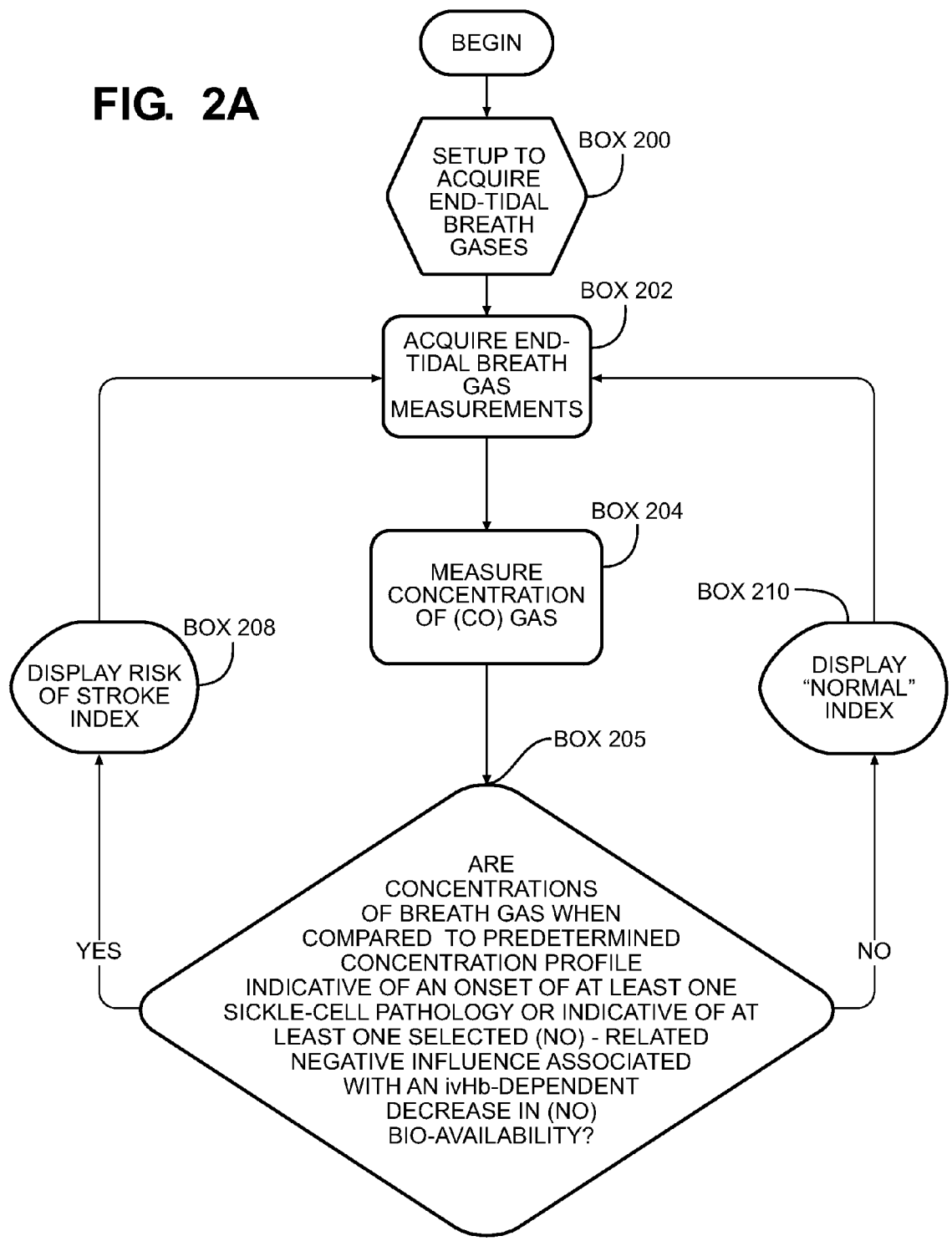

METHOD FOR PREDICTING STROKE AND PAIN IN A HUMAN PATIENT

CROSS-REFERENCE TO RELATED APPLICATIONS

The present application is related to, and claims priority from, U.S. Provisional Patent Application No. 60/540,146 filed on Jan. 29, 2004, herein incorporated by reference, and U.S. Provisional Patent Application No. 60/540,242 filed on Jan. 29, 2004, herein also incorporated by reference.

TECHNICAL FIELD

The present invention is related generally to methods for diagnosing and predicting the occurrence of stroke or pain in a human patient, and in particular, to a method for the detection of a specific pre-condition to stroke or pain by measuring hemolysis indicators such as bilirubin, carbon monoxide (CO), or nitrous-oxide (NO).

BACKGROUND ART

Sickle Cell Anemia is a disease which affects over 70,000 people in the United States of America and is the result of a point mutation in a single amino acid of hemoglobin. The mutated hemoglobin is referred to as Hemoglobin S (HbS). When HbS binds oxygen in a red blood cell, it precipitates, forming crystals that damage membranes in red blood cells, causing the red blood cells to lyse, releasing HbS into plasma, and lowering red blood cell levels (anemia). In severe cases in which this hemolysis results in a crisis of low oxygen tension, death can be the end point. It has been found that the binding of the vasorelaxant hormone, nitric oxide (NO), by HbS after it is released from red blood cells is 1000 times more efficient than the binding by normal Hb, lowering levels of "free" NO to a point at which severe vaso-constriction occurs. The lowered blood flow to tissues is thought to be a primary cause of severe bouts of pain in patients.

It is believed that released HbS is normally metabolized (catabolized) by 'intravascular' hemolysis processes. This process is different than 'extra vascular' hemolysis occurring during neonatal jaundice in which the abnormal red blood cells are recognized by RES cells and phagocytosed, 'before' Hb is released within the phagocyte and then heme is released prior to reaction with heme oxygenase, releasing (CO). The intravascular hemolysis processes include the binding of Hb to plasma proteins ("haptoglobins"), and the complex of Hb/haptoglobin is carried to the RES where heme is released to generate (CO). During intravascular hemolysis, some heme can be released in plasma and the free heme is bound by another protein (hemopexin), which carries the heme to the liver, where liver heme oxygenase generates the (CO).

It would be advantageous to identify (CO) measurements (e.g. via hemolysis screener) as a sensitive indicator of an abnormal level of hemolysis (intravascular and/or extra vascular) before the plasma levels of HbS reach a point at which enough NO is bound to cause vasocontrictive-dependent pain or more severe pathologies, such as a stroke, which can lead to death. This would permit Sickle Cell Anemia patients to be regularly screened for (CO) in an emergency room, hospital bedside, doctors' office, or home, etc. The urgency of action in response to high (CO) levels might vary from more intense monitoring of patients, to increasing treatment (e.g. with (NO)), to more intensive critical care.

Currently, a common clinical practice to help persons with sickle-cell anemia is a blood transfusion, often performed on a monthly basis. However, the timing of these transfusions is often solely based on the timing of the last transfusion, and not based on a clinical predictor of pain. The transfusions themselves are a source of trauma and pain to the patient, and are often very costly. Even if all these other disadvantages are addressed, often transfusions are not possible because blood is not available.

Thus, it is highly desirable to minimize the necessity of transfusions, by the detection of predictors, such as carbon monoxide (CO), from sickle-cell anemia related pathologies, such as hemolysis, that eventually lead to negative clinical effects, such as pain, anemia and increased risk of stroke, infection and deafness.

Accordingly, there is a need for an accurate and reliable method for predicting the onset of pain and/or the onset of a stroke in a human patient based on non-invasive measurements of blood gases or exhaled breath gases such as (CO).

SUMMARY OF THE INVENTION

Briefly stated, the present invention provides a method for predicting the onset of pain in a human patient by detecting abnormal levels of hemolysis, as indicated by the measurement of (CO).

In an alternate embodiment, the present invention provides a method for predicting the occurrence of a stroke in a human patient by detecting abnormal levels of hemolysis, as indicated by the measurement of (CO). In an alternate embodiment, the method of the present invention may be utilized to predict the onset of a variety of well-characterized pathologies of Sickle Cell Anemia.

In an alternate embodiment, the method of the present invention may be utilized limiting the occurrence and severity of deafness in Sickle Cell Anemia children.

The foregoing and other objects, features, and advantages of the invention as well as presently preferred embodiments thereof will become more apparent from the reading of the following description in connection with the accompanying drawings.

BRIEF DESCRIPTION OF THE DRAWINGS

In the accompanying drawings which form part of the specification:

FIGS. 2 and 2A are flow charts illustrating the steps in methods of the present invention for continuously monitoring a patient to predict the occurrence of strokes.

Corresponding reference numerals indicate corresponding parts throughout the several figures of the drawings.

BEST MODE FOR CARRYING OUT THE INVENTION

Figure 1:
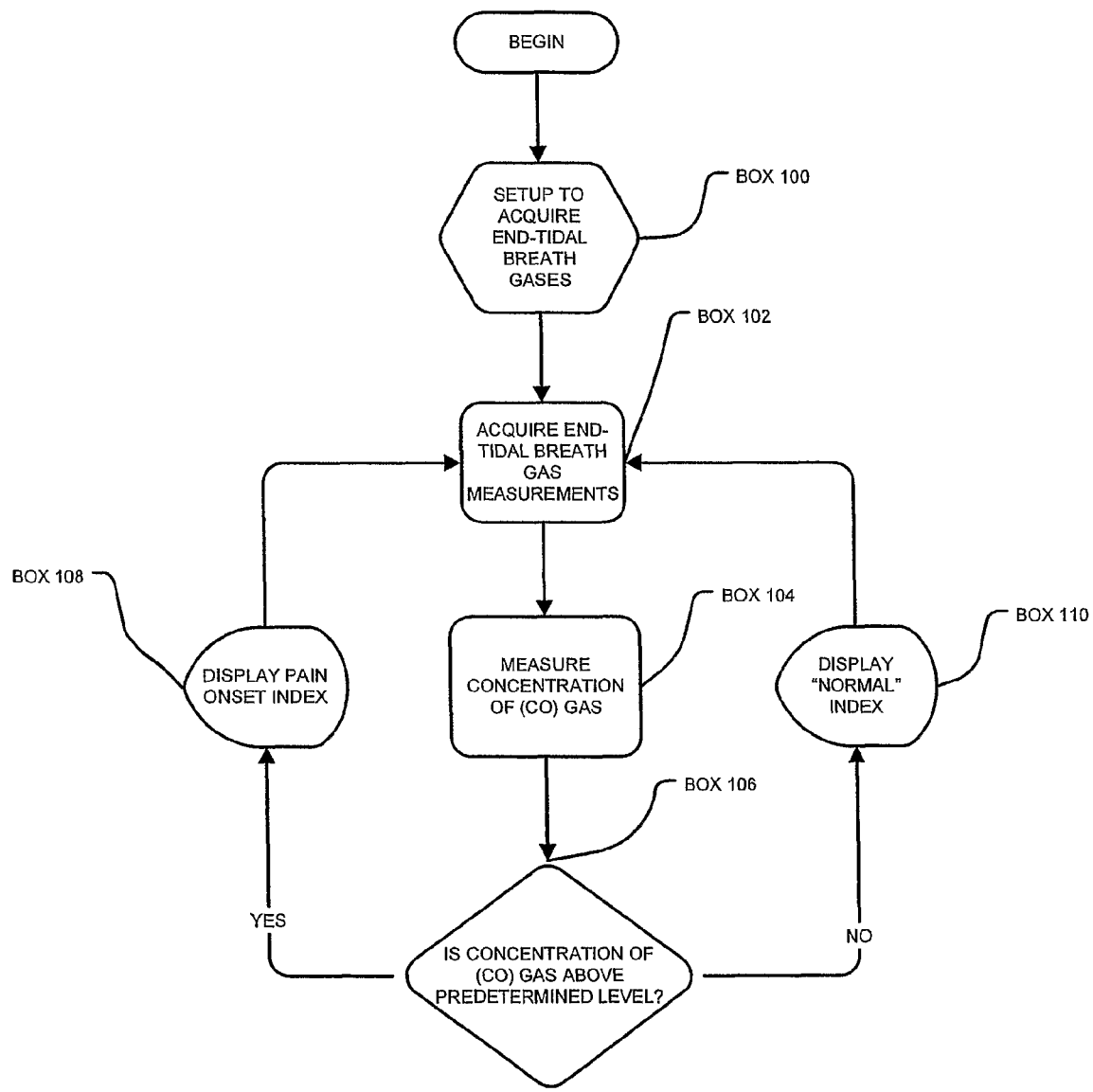
FIGS. 1 and 1A are flow charts illustrating the steps in methods of the present invention for continuously monitoring a patient for the onset of pain.

The following detailed description illustrates the invention by way of example and not by way of limitation. The description clearly enables one skilled in the art to make and use the invention, describes several embodiments, adaptations, variations, alternatives, and uses of the invention, including what is presently believed to be the best mode of carrying out the invention.

A first method of the present invention may be utilized to predict when persons with Sickle Cell Anemia are at risk of experiencing pain in the near-term future. By being aware that pain is likely to occur, persons with Sickle Cell Anemia and/or their caregivers will be better able to take actions to limit the impacts of the pain (e.g. disruption in routine activities), plan for the type and timing of prophylactic treatment to limit the amount of pain, and prepare for therapeutic treatment used later at the onset and during the experience of pain.

A second method of the present invention may be utilized to predict when persons with Sickle Cell Anemia are at risk of experiencing a stroke in the near-term future. By being aware that a stroke is likely to occur, persons with Sickle Cell Anemia and/or their caregivers will be better able to take actions to limit the impacts of the stroke (e.g. disruption in routine activities), plan for the type and timing of prophylactic treatment to reduce the risk for stroke occurrence, and prepare for therapeutic treatment used later at the onset and during a stroke.

The foundation of the methods of the present invention is the discovery that intravascular hemoglobin (e.g. from hemolysis) decreases bioavailability of nitrous-oxide (NO), which causes events such as vasoconstriction, commonly associated with creating pain and reducing oxygen tension in the brain. Strokes are associated with low oxygen tension in the brain. Patients with Sickle Cell Anemia have abnormal hemoglobin, hemoglobin-S (HbS). The presence of HbS in erythrocytes (red blood cells) causes destabilization of the red blood cells, which causes lyses and release of hemoglobin in the blood's plasma fraction ("intravascular hemoglobin").

Hemolysis of sRBCs would be expected to decrease, not increase, occlusion-dependent mechanisms of pathologies. However, in the NO-based mechanisms of pathologies (e.g. pain), hemolysis is a necessary prerequisite for formation of intravascular hemoglobin (ivHb), which is necessary to reduce NO-bioavailability, which was recently discovered to be associated with causing pathologies (e.g. pain).

Previously, experts believed that most, if not all, Sickle Cell Anemia related pain was caused by the clumping of abnormally-shaped ("sickle"-shaped) red blood cells, and that clumping was thought to 'block' blood vessels, resulting in pain and the occurrence of strokes. This prior belief in the clumping causation was independent of whether hemolysis was occurring. Recent evidence indicates much of the Sickle Cell Anemia-related pain and increased risk of stroke may be a result of this newly-discovered role of hemolysis and the subsequent elevation of intravascular hemoglobin in reducing (NO) bioavailability.

Bilirubin and (CO) are produced in equal amounts from metabolism of heme, which is produced from metabolism of hemoglobin, including from intravascular hemoglobin derived from hemolysis. Because it is the intravascular hemoglobin that causes a decrease in (NO) bioavailability and subsequent pain or increased risk of stroke, the question arises as to whether enough intravascular hemoglobin is metabolized such that (CO) will be detectable before the onset of pain or the occurrence of a stroke.

While it has been observed that at certain stages of hemolysis, measurable bilirubin can be elevated 'without' the subsequent occurrence of pain or stroke in the patient, It is very likely that elevated levels of (CO) from hemolysis, present 'before' the onset of pain or the occurrence of a stroke, will be within the detection limits of existing detection methods and devices with little or no device modifications.

The exact profile of elevated (CO) to predict pain or the occurrence of a stroke can be defined from clinical research. Within a patient, natural hemoglobin Sickle Cell Anemia scavenging systems involve normal processes for removal of intravascular hemoglobin. These normal systems are expected to produce elevated (CO), for some period of time and at some level of (CO), while maintaining levels of intravascular hemoglobin below a threshold that results in a pain or stroke-causing decrease in (NO) bioavailability. However, a duration and level of elevated (CO) exists that is predictive of future pain or the occurrence of a stroke, and that duration and level will be precisely defined from results of clinical research.

The normal system for removal of intravascular hemoglobin will prevent reduction of (NO) for some duration of time, despite the appearance of elevated (CO) levels, but, later, the removal system can be overwhelmed and (NO) decreases, resulting in pathologies. The precise profiles of elevated (CO) (duration, levels) that correlate with the presence of each pathology will define the exact specifications for detection devices employing the methods of the present invention.

Turning to FIG. 1, a first method of the present invention involves the detection of (CO) gas in a patient's breath, e.g. expired (CO) gas, from hemolysis, which is used to predict the onset of pain. The first method of the present invention relies on the association between hemolysis and a reduction in bioavailability of nitric oxide (NO), which leads to pain by mechanisms that include vasoconstriction. To continuously monitor a patient for the onset of pain, for example, in patient confined to a hospital bed, the patient is provided with suitable means to capture end-tidal breath gases for analysis. (Box 100). These may include the use of any conventional breath gas analyzer system having sufficient sensitivity to acquire measurements of gas concentrations required by the present invention. The end-tidal breath gas measurements are then acquired (Box 102), and the specific concentration of the expired (CO) gas is measured (Box 104). If the concentration exceeds the predetermined limits found to indicate the onset of pain in the patient (Box 106), a warning or other pain onset index is displayed to an operator or presented on a monitoring station (Box 108). Alternatively, if the concentration does not indicate the onset of pain, a "normal" indicator is displayed (Box 110).

Figure 2:
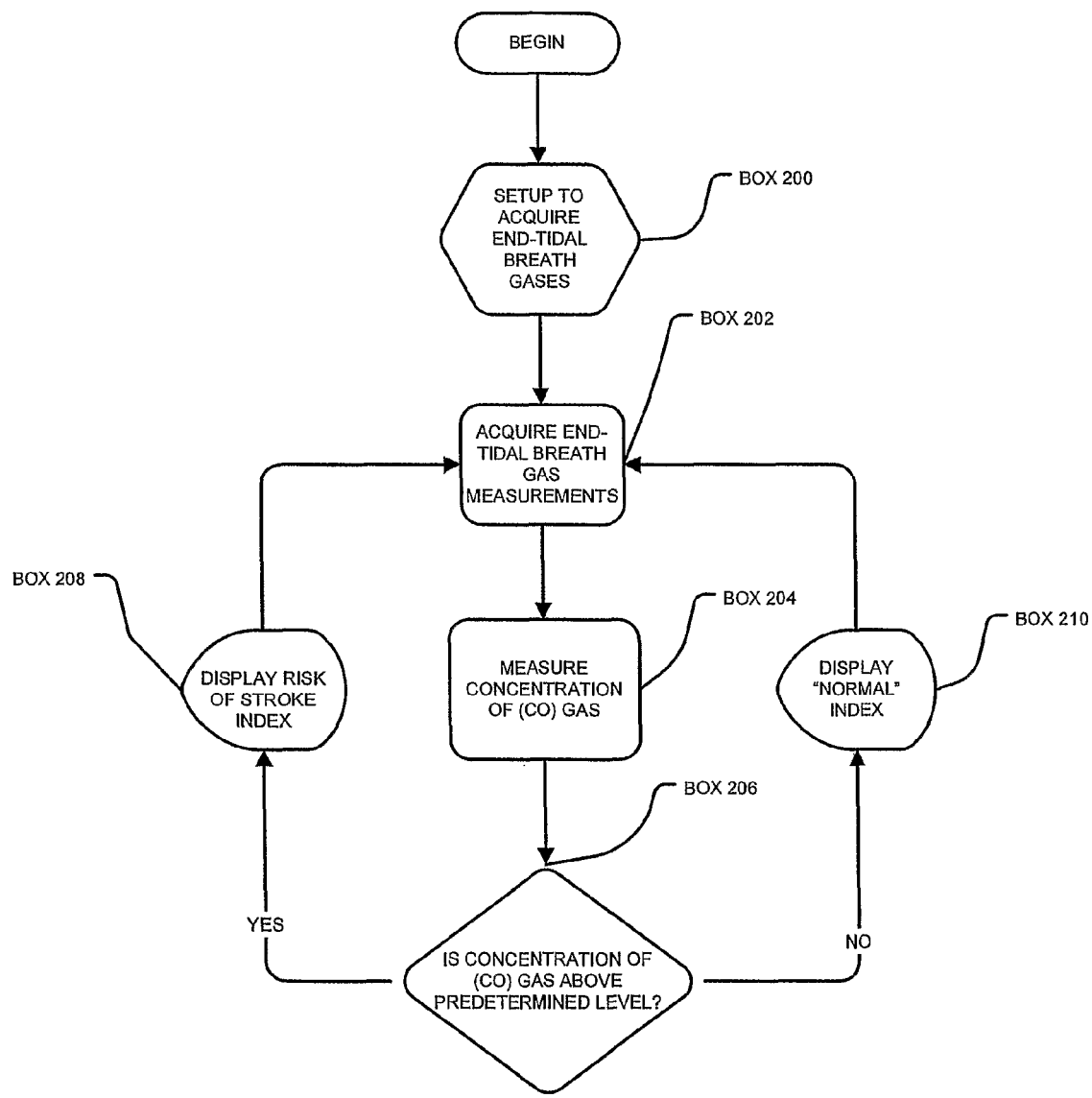

Turning to FIG. 2, a second method of the present invention involves the detection of (CO) gas in a patient's breath, e.g. expired (CO) gas, from hemolysis, which is used to predict the occurrence of strokes. The second method of the present invention relies on the association between hemolysis and a reduction in bioavailability of nitric oxide (NO), which leads to pain by mechanisms that include vasoconstriction. To continuously monitor a patient for the onset of a stroke, for example, in patient confined to a hospital bed, the patient is provided with suitable means to capture end-tidal breath gases for analysis. (Box 200). These may include the use of any conventional breath gas analyzer system having sufficient sensitivity to acquire measurements of gas concentrations required by the present invention. The end-tidal breath gas measurements are then acquired (Box 202), and the specific concentration of the expired (CO) gas is measured (Box 204). If the concentration exceeds the predetermined limits found to indicate the onset of pain in the patient (Box 16), a warning or other stroke onset index is displayed to an operator or on a monitoring station (Box 208). Alternatively, if the concentration does not indicate the likelihood of the onset of a stroke, a "normal" indicator is displayed (Box 210).

Figure 1A:
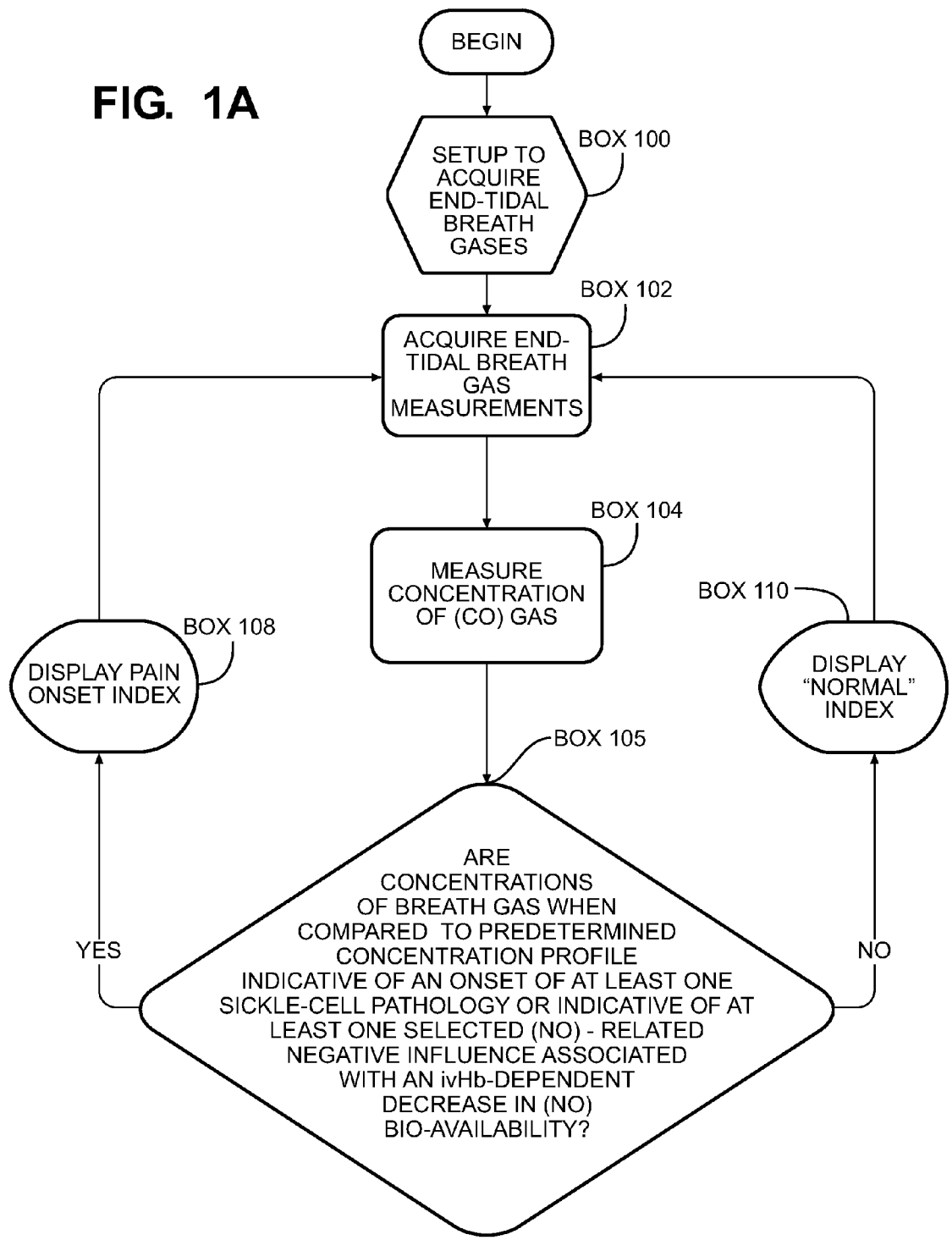

The process of acquiring end-tidal breath gas measurements and measuring the concentration of (CO) gas for comparison with predetermined levels in either method may be repeated continuously, such as for patients coupled to respirator systems. The steps illustrated in FIGS. 1A and 2A include comparing the measured concentrations of breath gas to a predetermined concentration profile indicative of an onset of at least one sickle-cell pathology or indicative of at least one selected nitric oxide-related negative influence associated with an ivHb-dependent decrease in bioavailability.

Those of ordinary skill in the art will recognize that measurements of the gas levels in a patient's breath may be provided as input to a computer configured with suitable software application for gas level analysis, generating one or more indices representative of the likely onset of pain, the likely occurrence of stroke, or other related conditions in the patient. These indices may be discrete values, or may be displayed to an operator in the form of a graphical representation.

The methods of the present invention for the prediction of the onset of pain or the occurrence of a stroke in a human patient may be utilized with any device capable of measuring the levels of carbon monoxide (CO) produced in the patient as a result of hemolysis, including devices for measuring breath end-tidal (CO) levels. Since the methods of the present invention for predicting the onset of pain and the likely occurrence of stroke are non-invasive, they may be used many times, even daily, or multiple times each day, possibly throughout the life-time of a patient without affecting the patient.

An alternate method of the present invention predicts a condition referred to as "sudden deafness", which may result from a neurotoxicity, and which also occurs in persons with Sickle Cell Anemia. Published research, dating back to the 1970s, on children with Sickle Cell Anemia, report "sudden deafness". However, no clear explanation has been reported for why sudden deafness occurs in Sickle Cell Anemia children. Although sudden deafness may involve some role of decreased nitrous-oxide bioavailability, it is believed that sudden deafness in Sickle Cell Anemia children is at least partially the result of a metabolic product of hemolysis, i.e. bilirubin. Recent research results from studies of jaundiced newborns has provided strong evidence for bilirubin causing a variety of neurotoxicities, and the first neurotoxicity that becomes evident in jaundiced newborns is damage to auditory nerves. Bilirubin levels in a patient are elevated as a result of heme metabolism of hemoglobin after the hemolysis that characterizes the disease of Sickle Cell Anemia. Because bilirubin and (CO) are produced in equal amounts from heme, measuring (CO) by the method of the present invention further provides a useful alternative method for predicting a risk of deafness due to damage to auditory nerve from neurotoxic levels of bilirubin.

In alternate embodiments, the method of the present invention is further useful in predicting a wide range of sickle-cell anemia related pathologies, e.g. anemia, stroke, or infection, are additionally caused by a decreased (NO) bioavailability, as well as any other (NO)-related negative influences of hemolysis, chronic hereditary hemolytic diseases including pulmonary hypertension, cutaneous ulceration and renal failure, acute hemolytic crises including thrombotic thrombocytopenic purpura, malaria, hemolysis from cardiopulmonary bypass procedures, transfusion of aged blood, myoglobinuria after muscle infarction, intravascular thrombosis, and ischemic central nervous system events. Other hemolytic conditions (e.g. malaria) likely have one or more pathologies that are created or worsened by an ivHb-dependent decrease in NO-bioavailability, and hence may be predicted utilizing the methods of the present invention. The 'level' of elevated ivHb and the 'duration' of elevated ivHB will vary with each different hemolytic condition. For example, ivHb levels relative to hemolysis rates (e.g. via CO measures) will vary with the nature of hemolysis. For example, SCA hemolysis occurs primarily intravascularly, but some other hemolytic conditions occur primarily extravascularly, such as in the Reticulo-Endothelial System (RES), which is the situation with jaundice in neonates. Other hemolytic conditions may involve both intravascular hemolysis and extra vascular hemolysis. Additionally, the relationship between CO and NO-dependent pathologies will be affected by the hemoglobin savaging system, which involves normal processes for removal of ivHb. This normal system is expected to produce elevated CO, for some period of time and at some level of CO, while maintaining levels of ivHB below a threshold that results in a decrease in NO bioavailability. The exact profile of elevated CO to predict pain/stroke/other pathologies will be defined by clinical research. A unique CO profile will be identified to predict each NO-dependent pathology for each hemolytic condition.

The method of the present invention may be utilized to assist in the care of any persons with acute or chronic hemolytic diseases or conditions, especially in instances associated with elevated levels of intravascular hemoglobin.

These benefits are expected to result in better efficacy of medical interventions with less side effects, providing secondary benefits in improved quality of life, duration of life, and reduced medical costs, including costs associated with caring for serious health problems associated with pain crises.

The present invention can be embodied in-part in the form of computer-implemented processes and apparatuses for practicing those processes. The present invention can also be embodied in-part in the form of computer program code containing instructions embodied in tangible media, such as floppy diskettes, CD-ROMs, hard drives, or an other computer readable storage medium, wherein, when the computer program code is loaded into, and executed by, an electronic device such as a computer, micro-processor or logic circuit, the device becomes an apparatus for practicing the invention.

The present invention can also be embodied in-part in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented in a general-purpose microprocessor, the computer program code segments configure the microprocessor to create specific logic circuits.

In view of the above, it will be seen that the several objects of the invention are achieved and other advantageous results are obtained. As various changes could be made in the above constructions without departing from the scope of the invention, it is intended that all matter contained in the above description or shown in the accompanying drawings shall be interpreted as illustrative and not in a limiting sense.

The invention claimed is:

1. A method for predicting the onset of at least one nitric oxide-related negative influence in a human patient, said method comprising:
providing an electronic device;
measuring a concentration level of at least one breath gas exhaled by the patient over a period of time;
comparing the measured concentration levels with a predetermined concentration profile indicative of an onset of at least one selected nitric oxide-related negative influence; and
wherein said at least one selected nitric oxide-related negative influence is associated with an intravascular hemoglobin-dependent decrease in nitric oxide bioavailability, wherein said step of comparing is carried out by the electronic device.

2. The method of claim 1 wherein said nitric oxide-related negative influence includes nitric oxide-related negative influences of hemolysis in a human patient and nitric oxide-related negative influences of chronic hereditary hemolytic disease in a human patient.

3. The method of claim 2 wherein said one or more nitric oxide-related negative influences of chronic hereditary hemolytic disease include one or more pathologies from a set of pathologies including pulmonary hypertension, cutaneous ulceration, renal failure, thrombotic thrombocytopenic purpura, and malaria.

\* \* \* \* \*